United States Patent
Sørensen et al.

(10) Patent No.: US 8,048,877 B2
(45) Date of Patent: Nov. 1, 2011

(54) GUANIDINE DERIVATIVES AND THEIR MEDICAL USE

(75) Inventors: Ulrik Svane Sørensen, Søborg (DK); Birgitte L. Eriksen, Farum (DK); Lene Teuber, Værløse (DK); Dan Peters, Malmö (SE); Dorte Strøbæk, Farum (DK); Tina Holm Johansen, Smørum (DK); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 488 days.

(21) Appl. No.: 12/279,928

(22) PCT Filed: Mar. 22, 2007

(86) PCT No.: PCT/EP2007/052747
§ 371 (c)(1),
(2), (4) Date: Aug. 19, 2008

(87) PCT Pub. No.: WO2007/110363
PCT Pub. Date: Oct. 4, 2007

(65) Prior Publication Data
US 2009/0099208 A1    Apr. 16, 2009

(30) Foreign Application Priority Data
Mar. 24, 2006  (DK) .................................. 2006 00421

(51) Int. Cl.
*A61K 31/55*   (2006.01)
*C07D 243/04*  (2006.01)

(52) U.S. Cl. ........................................ 514/218; 540/553
(58) Field of Classification Search ..................... None
See application file for complete search history.

(56) References Cited

U.S. PATENT DOCUMENTS

| 4,369,325 | A | 1/1983 | Toldy et al. |
| 5,604,228 | A | 2/1997 | Keana et al. |
| 6,194,447 | B1 | 2/2001 | Jensen et al. |
| 7,067,507 | B2 * | 6/2006 | Pulley et al. .................. 514/183 |

FOREIGN PATENT DOCUMENTS

| GB | 869181 | 5/1961 |
| WO | WO-95/20950 A1 | 8/1995 |

OTHER PUBLICATIONS

Jantzen and Robinson. Modern Pharmaceutics, 1996, p. 596.*
Sailer et al., Mol. Cell. Neurosci. 2004 26 pp. 458-469.
Liegeois J-F et al., Current Medicinal Chemistry 2003, 10, pp. 625-647.
Struve et al., J. Org. Chem. 1977 42 (25) p. 4035-4040.

* cited by examiner

*Primary Examiner* — Noble Jarrell
(74) *Attorney, Agent, or Firm* — Birch, Stewart, Kolasch & Birch, LLP

(57) ABSTRACT

This invention relates to novel guanidine derivatives useful as modulators of small-conductance calcium-activated potassium channels (SK channels). In other aspects the invention relates to the use of these compounds in a method for therapy and to pharmaceutical compositions comprising the compounds of the invention.

10 Claims, No Drawings

GUANIDINE DERIVATIVES AND THEIR MEDICAL USE

TECHNICAL FIELD

This invention relates to novel guanidine derivatives useful as modulators of small-conductance calcium-activated potassium channels (SK channels). In other aspects the invention relates to the use of these compounds in a method for therapy and to pharmaceutical compositions comprising the compounds of the invention.

BACKGROUND ART

Three subtypes of small-conductance calcium-activated potassium channels (SK channels) have been cloned: SK1, SK2 and SK3 (corresponding to KCNN1-3 using the genomic nomenclature). The activity of these channels is determined by the concentration of free intracellular calcium ($[Ca^{2+}]_i$) via calmodulin that is constitutively bound to the channels. SK channels are tightly regulated by $[Ca^{2+}]_i$ in the physiological range being closed at $[Ca^{2+}]_i$ up to around 0.1 µM but fully activated at a $[Ca^{2+}]_i$ of 1 µM. Being selective for potassium, open or active SK channels have a hyperpolarizing influence on the membrane potential of the cell. SK channels are widely expressed in the central nervous system. The distribution of SK1 and SK2 show a high degree of overlap and display the highest levels of expression in neocortical, limbic and hippocampal areas in the mouse brain. In contrast, the SK3 channels show high levels of expression in the basal ganglia, thalamus and the brain stem monoaminergic neurons e.g. dorsal raphe, locus coeruleus and the ventral tegmental area (Sailer et al: "Comparative immunohistochemical distribution of three small-conductance $Ca^{2+}$-activated potassium channel subunits, SK1, SK2, and SK3 in mouse brain; *Mol. Cell. Neurosci.* 2004 26 458-469). The SK channels are also present in several peripheral cells including skeletal muscle, gland cells, liver cells and T-lymphocytes.

The hyperpolarizing action of active SK channels plays an important role in the control of firing pattern and excitability of excitable cells. SK channel inhibitors such as apamin and bicuculline-methobromide have been demonstrated to increase excitability whereas the opener 1-EBIO is able to reduce electrical activity. In non-excitable cells where the amount of $Ca^{2+}$ influx via voltage-independent pathways is highly sensitive to the membrane potential an activation of SK channels will increase the driving force whereas a blocker of SK channels will have a depolarising effect and thus diminish the driving force for calcium.

Based on the important role of SK channels in linking $[Ca^{2+}]_i$ and membrane potential, SK channels are an interesting target for developing novel therapeutic agents.

A review of SK channels and SK channel modulators may be found in Liegeois J-F et al.: "Modulation of small conductance calcium-activated potassium (SK) channels: a new challenge in medicinal chemistry", *Current Medicinal Chemistry* 2003 10 625-647.

Known modulators of SK channels suffer from being large molecules or peptides (e.g. apamin, scyllatoxin, tubocurarine, dequalinium chloride and UCL1684) or from having low potency (e.g. 1-EBIO and riluzole). Thus, there is a continued need for compounds with an optimized pharmacological profile. In particular, there is a great need for selective ligands, such as SK3 channel modulators.

Struve et al; *J. Org. Chem.* 1977 42 (25) 4035-4040 describe the synthesis of and structural assignments for some N-phosphono-2-iminoimidazolidines (cyclic guanidines). The compound 1,3-Dibenzyl-imidazolidin-2-ylideneamine is disclosed as an intermediate compound. A biological activity of this compound is, however, not reported.

SUMMARY OF THE INVENTION

In its first aspect, the invention provides guanidine derivatives of Formula I:

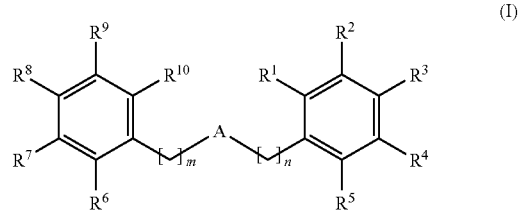

(I)

an isomer thereof or any mixture of its isomers, or a pharmaceutically acceptable salt thereof; wherein m and n, independently of each other, is 0, 1 or 2, provided, however, if m is 0 then n is not also 0;

A represents a linking group selected from II, III and IV:

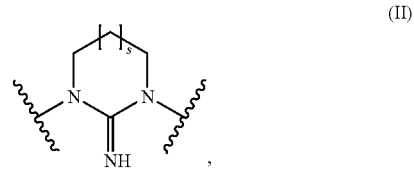

(II)

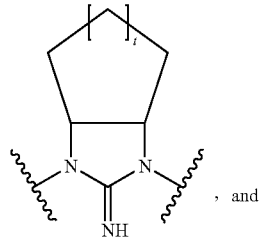

(III)

, and

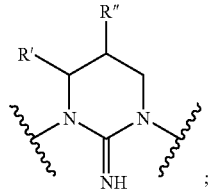

(IV)

;

wherein s is 0, 1 or 2;

t is 1, 2 or 3;

R' and R" together with the ring to which they are attached form a 6-membered fused benzo ring, which benzo ring may optionally be substituted one or more times with substituents selected from the group consisting of halo, trifluoromethyl, trifluoromethoxy, cyano, alkyl, hydroxy, alkoxy, N-alkyl-amino and N,N-dialkyl-amino; and $R^1$, $R^2$, $R^3$, $R^4$, $R^5$, $R^6$, $R^7$, $R^8$, $R^9$ and $R^{10}$, independently of each other, represent hydrogen, halo, trifluoromethyl, trifluoromethoxy, cyano, alkyl, hydroxy, alkoxy, N-alkyl-amino and/or N,N-dialkyl-amino, provided, however, that if A is a linking group II wherein s is 0, then at least one of $R^1$, $R^2$, $R^3$, R[4] and R[5] is different from hydrogen, and at least one of R[6], R[7], R[8], R[9] and R[10] is different from hydrogen.

In another aspect, the invention provides pharmaceutical compositions comprising a therapeutically effective amount of the guanidine derivative of the invention, or any of its isomers or any mixture of its isomers, or a pharmaceutically acceptable salt thereof, or a prodrug thereof, together with at least one pharmaceutically acceptable carrier, excipient or diluent.

Viewed from another aspect the invention relates to the use of the guanidine derivative of the invention, or any of its isomers or any mixture of its isomers, or a pharmaceutically acceptable salt thereof, for the manufacture of a medicament.

In yet another aspect the invention provides a method for treatment, prevention or alleviation of a disease or a disorder or a condition of a living animal body, including a human, which disorder, disease or condition is responsive to modulation of SK channels, which method comprises the step of administering to such a living animal body in need thereof a therapeutically effective amount of the guanidine derivative of the invention, or any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Guanidine Derivatives

In its first aspect, the invention provides guanidine derivatives of Formula I:

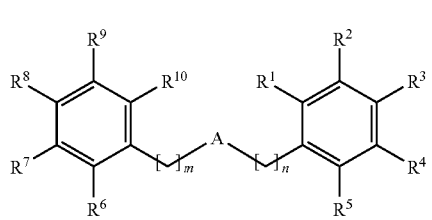

(I)

an isomer thereof or any mixture of its isomers, or a pharmaceutically acceptable salt thereof; wherein m and n, independently of each other, is 0, 1 or 2, provided, however, if m is 0 then n is not also 0;

A represents a linking group selected from II, III and IV:

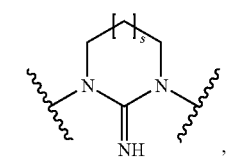

(II)

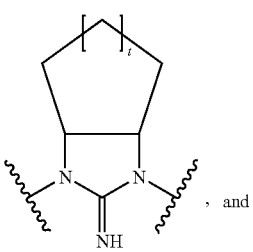

(III)

, and

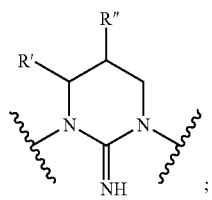

(IV)

wherein s is 0, 1 or 2;

t is 1, 2 or 3;

R' and R" together with the ring to which they are attached form a 6-membered fused benzo ring, which benzo ring may optionally be substituted one or more times with substituents selected from the group consisting of halo, trifluoromethyl, trifluoromethoxy, cyano, alkyl, hydroxy, alkoxy, N-alkyl-amino and N,N-dialkyl-amino; and R[1], R[2], R[3], R[4], R[5], R[6], R[7], R[8], R[9] and R[10], independently of each other, represent hydrogen, halo, trifluoromethyl, trifluoromethoxy, cyano, alkyl, hydroxy, alkoxy, N-alkyl-amino and/or N,N-dialkyl-amino, provided, however, that if A is a linking group II wherein s is 0, then at least one of R[1], R[2], R[3], R[4] and R[5] is different from hydrogen, and at least one of R[6], R[7], R[8], R[9] and R[10] is different from hydrogen.

In a preferred embodiment the guanidine derivatives of the invention is a compound of Formula I, wherein m and n, independently of each other, is 0, 1 or 2, provided, however, if m is 0 then n is not also 0.

In a more preferred embodiment one of m and n is 0, 1 or 2; and the other of m and n is 1 or 2.

In another more preferred embodiment one of m and n is 0 or 1; and the other of m and n is 1.

In a third more preferred embodiment m and n both represent 1.

In a fourth more preferred embodiment m represents 1; and n represents 0.

In another preferred embodiment the guanidine derivatives of the invention is a compound of Formula I, wherein A represents a linking group selected from II, III and IV:

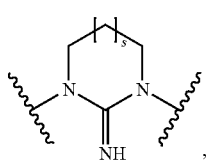

(II)

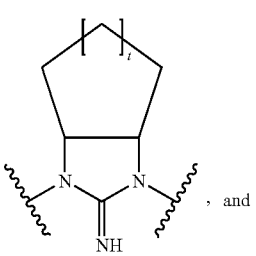

(III)

, and

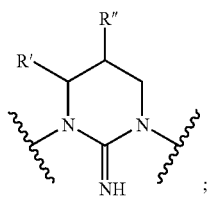

(IV)

wherein s is 0, 1 or 2;

t is 1, 2 or 3; and

R' and R" together with the ring to which they are attached form a 6-membered fused benzo ring, which benzo ring may optionally be substituted one or more times with substituents selected from the group consisting of halo, trifluoromethyl, trifluoromethoxy, cyano, alkyl, hydroxy, alkoxy, N-alkyl-amino and N,N-dialkyl-amino.

In a more preferred embodiment A represents

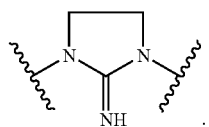

In another more preferred embodiment A represents

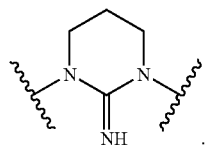

In a third more preferred embodiment A represents

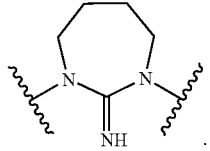

In a fourth more preferred embodiment A represents

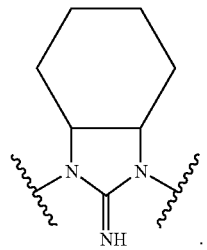

In a fifth more preferred embodiment A represents

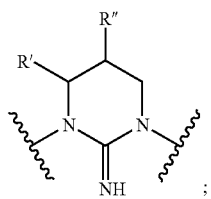

wherein R' and R" together with the ring to which they are attached form a 6-membered fused benzo ring, which benzo ring may optionally be substituted one or more times with substituents selected from the group consisting of halo, trifluoromethyl, trifluoromethoxy, cyano, alkyl, hydroxy, alkoxy, N-alkyl-amino and N,N-dialkyl-amino.

In a more preferred embodiment R' and R" together with the ring to which they are attached form a 6-membered fused benzo ring, which benzo ring may optionally be substituted one or more times with substituents selected from the group consisting of halo, trifluoromethyl, trifluoromethoxy and cyano.

In an even more preferred embodiment R' and R" together with the ring to which they are attached form a 6-membered fused benzo ring, which benzo ring may optionally be substituted four times with halo, in particular fluoro or chloro.

In another more preferred embodiment R' and R" together with the ring to which they are attached form a 6-membered fused benzo ring, which benzo ring may optionally be substituted one or two times with substituents selected from the group consisting of halo, trifluoromethyl, trifluoromethoxy, cyano, alkyl, hydroxy, alkoxy, N-alkyl-amino and N,N-dialkyl-amino.

In a third preferred embodiment the guanidine derivatives of the invention is a compound of Formula I, wherein $R^1$, $R^2$, $R^3$, $R^4$, $R^5$, $R^6$, $R^7$, $R^8$, $R^9$ and $R^{10}$, independently of each other, represent hydrogen, halo, trifluoromethyl, trifluoromethoxy, cyano, alkyl, hydroxyl, alkoxy, N-alkyl-amino and/or N,N-dialkyl-amino.

In a more preferred embodiment $R^1$, $R^2$, $R^3$, $R^4$, $R^5$, $R^6$, $R^7$, $R^8$, $R^9$ and $R^{10}$, independently of each other, represent hydrogen, halo, trifluoromethyl, trifluoromethoxy, cyano, alkyl and/or alkoxy.

In an even more preferred embodiment $R^1$, $R^2$, $R^3$, $R^4$, $R^5$, $R^6$, $R^7$, $R^8$, $R^9$ and $R^{10}$, independently of each other, represent halo, trifluoromethyl, trifluoromethoxy, cyano, alkyl and/or alkoxy.

In a yet more preferred embodiment $R^1$, $R^2$, $R^3$, $R^4$, $R^5$, $R^6$, $R^7$, $R^8$, $R^9$ and $R^{10}$ all represent hydrogen.

In one particularly preferred embodiment one of $R^1$, $R^2$, $R^3$, $R^4$ and $R^5$, and one of $R^6$, $R^7$, $R^8$, $R^9$ and $R^{10}$, independently of each other, represent halo, trifluoromethyl, trifluoromethoxy, cyano, alkyl and/or alkoxy; and the remaining of $R^1$, $R^2$, $R^3$, $R^4$ and $R^5$, and $R^6$, $R^7$, $R^8$, $R^9$ and $R^{10}$ represent hydrogen.

In a third more preferred embodiment $R^1$ and $R^6$, independently of each other, represent halo, trifluoromethyl, trifluoromethoxy, cyano, alkyl and/or alkoxy; and $R^2$, $R^3$, $R^4$, $R^5$, $R^7$, $R^8$, $R^9$ and $R^{10}$ represent hydrogen.

In a fourth more preferred embodiment $R^2$ and $R^7$, independently of each other, represent halo, trifluoromethyl, trifluoromethoxy, cyano, alkyl and/or alkoxy; and $R^1$, $R^3$, $R^4$, $R^5$, $R^6$, $R^8$, $R^9$ and $R^{10}$ represent hydrogen.

In a fifth more preferred embodiment $R^3$ and $R^8$, independently of each other, represent halo, trifluoromethyl, trifluoromethoxy, cyano, alkyl and/or alkoxy; and $R^1$, $R^2$, $R^4$, $R^5$, $R^6$, $R^7 R^9$ and $R^{10}$ represent hydrogen.

In another particularly preferred embodiment two of $R^1$, $R^2$, $R^3$, $R^4$ and $R^5$, and two of $R^6$, $R^7$, $R^8$, $R^9$ and $R^{10}$, independently of each other, represent halo, trifluoromethyl, trifluoromethoxy, cyano, alkyl and/or alkoxy; and the remaining of $R^1$, $R^2$, $R^3$, $R^4$ and $R^5$, and $R^6$, $R^7$, $R^8$, $R^9$ and $R^{10}$ represent hydrogen.

In a more preferred embodiment $R^1$, $R^2$, $R^6$ and $R^7$, independently of each other, represent halo, trifluoromethyl, trifluoromethoxy, cyano, alkyl and/or alkoxy; and $R^3$, $R^4$, $R^5$, $R^8$, $R^9$ and $R^{10}$ all represent hydrogen.

In another more preferred embodiment $R^1$, $R^5$, $R^6$, and $R^{10}$, independently of each other, represent halo, trifluoromethyl, trifluoromethoxy, cyano, alkyl and/or alkoxy; and $R^2$, $R^3$, $R^4$, $R^7$, $R^8$ and $R^9$ all represent hydrogen.

In a third more preferred embodiment $R^2$, $R^5$, $R^7$, and $R^{10}$, independently of each other, represent halo, trifluoromethyl, trifluoromethoxy, cyano, alkyl and/or alkoxy; and $R^1$, $R^3$, $R^4$, $R^6$, $R^8$ and $R^9$ all represent hydrogen.

In a fourth more preferred embodiment $R^2$, $R^4$, $R^7$, and $R^9$, independently of each other, represent halo, trifluoromethyl, trifluoromethoxy, cyano, alkyl and/or alkoxy; and $R^1$, $R^3$, $R^5$, $R^6$, $R^8$ and $R^{10}$ all represent hydrogen.

In a fifth more preferred embodiment $R^2$, $R^3$, $R^7$ and $R^8$, independently of each other, represent halo, trifluoromethyl, trifluoromethoxy, cyano, alkyl and/or alkoxy; and $R^1$, $R^4$, $R^5$, $R^6$, $R^9$ and $R^{10}$ and all represent hydrogen.

In a sixth more preferred embodiment $R^2$, $R^3$, $R^7$ and $R^8$ all represent halo, in particular fluoro, chloro, bromo or iodo; and $R^1$, $R^4$, $R^5$, $R^9$ and $R^{10}$ all represent hydrogen.

In a seventh more preferred embodiment $R^2$, $R^3$, $R^7$ and $R^8$ all represent fluoro or chloro; and $R^1$, $R^4$, $R^5$, $R^6$, $R^9$ and $R^{10}$ all represent hydrogen.

In a more preferred embodiment $R^1$, $R^4$, $R^6$ and $R^9$, independently of each other, represent halo, trifluoromethyl, trifluoromethoxy, cyano, alkyl and/or alkoxy; and $R^2$, $R^3$, $R^5$, $R^7$, $R^8$ and $R^{10}$ all represent hydrogen.

In an even more preferred embodiment $R^1$ and $R^6$ both represent alkoxy, in particular methoxy; $R^4$ and $R^9$ both represent trifluoromethoxy; and $R^2$, $R^3$, $R^5$, $R^7$, $R^8$ and $R^{10}$ all represent hydrogen.

In a third particularly preferred embodiment three of $R^1$, $R^2$, $R^3$, $R^4$ and $R^5$, and three of $R^6$, $R^7$, $R^8$, $R^9$ and $R^{10}$, independently of each other, represent halo, trifluoromethyl, trifluoromethoxy, cyano, alkyl and/or alkoxy; and the remaining of $R^1$, $R^2$, $R^3$, $R^4$ and $R^5$, and $R^6$, $R^7$, $R^8$, $R^9$ and $R^{10}$ represent hydrogen.

In a more preferred embodiment $R^1$, $R^2$, $R^3$, $R^6$, $R^7$ and $R^8$, independently of each other, represent halo, trifluoromethyl, trifluoromethoxy, cyano, alkyl and/or alkoxy; and $R^4$, $R^5$, $R^9$ and $R^{10}$ all represent hydrogen.

In another more preferred embodiment $R^2$, $R^3$, $R^4$, $R^7$, $R^8$ and $R^9$, independently of each other, represent halo, trifluoromethyl, trifluoromethoxy, cyano, alkyl and/or alkoxy; and $R^1$, $R^5$, $R^6$, and $R^{10}$ all represent hydrogen.

In a third more preferred embodiment $R^1$, $R^3$, $R^4$, $R^6$, $R^8$ and $R^9$, independently of each other, represent halo, trifluoromethyl, trifluoromethoxy, cyano, alkyl and/or alkoxy; and $R^2$, $R^5$, $R^7$, and $R^{10}$ all represent hydrogen.

In a more preferred embodiment $R^1$, $R^3$, $R^4$, $R^6$, $R^8$ and $R^9$ all represent halo, in particular fluoro or bromo; and $R^2$, $R^5$, $R^7$ and $R^{10}$ all represent hydrogen.

In an even more preferred embodiment $R^1$ and $R^6$ both represent bromo; $R^3$, $R^4$, $R^8$ and $R^9$ all represent fluoro; and $R^2$, $R^5$, $R^7$ and $R^{10}$ all represent hydrogen.

In a fourth more preferred embodiment $R^1$, $R^3$, $R^5$, $R^6$, $R^8$ and $R^{10}$, independently of each other, represent halo, trifluoromethyl, trifluoromethoxy, cyano, alkyl and/or alkoxy; and $R^2$, $R^4$ $R^7$, and $R^9$ all represent hydrogen.

In a fifth more preferred embodiment $R^1$, $R^4$, $R^5$, $R^6$, $R^9$ and $R^{10}$, independently of each other, represent halo, trifluoromethyl, trifluoromethoxy, cyano, alkyl and/or alkoxy; and $R^2$, $R^3$, $R^7$ and $R^8$ and all represent hydrogen.

In a most preferred embodiment the guanidine derivatives of the invention is 1,3-Bis-(3,4-difluorobenzyl)imidazolidin-2-ylideneamine;
1,3-Bis-(3,4-dichlorobenzyl)imidazolidin-2-ylideneamine;
1,3-Bis-(3,4-difluorobenzyl)-3,4-dihydro-1H-quinazolin-2-ylideneamine;
(±)-trans-1,3-Bis-(3,4-difluoro-benzyl)octahydro-benzoimidazol-2-ylideneamine;
1,3-Bis-(4-fluorobenzyl)imidazolidin-2-ylideneamine;
1,3-Bis-(3,4-difluorobenzyl)tetrahydropyrimidin-2-ylideneamine;
1,3-Bis-(3-trifluoromethyl-benzyl)imidazolidin-2-ylideneamine;
1,3-Bis-(2-bromo-4,5-difluorobenzyl)-3,4-dihydro-1H-quinazolin-2-ylideneamine;
1,3-Bis-(2-bromo-4,5-difluorobenzyl)imidazolidin-2-ylideneamine;
1-(3,4-Difluorobenzyl)-3-phenyl-imidazolidin-2-ylideneamine;
1,3-Bis-(2,4,5-trifluorobenzyl)imidazolidin-2-ylideneamine;
1,3-Bis-(3,4-difluorobenzyl)-[1,3]diazepan-2-ylideneamine;
1,3-Bis-(3-trifluoromethoxybenzyl)imidazolidin-2-ylideneamine; or
1,3-Bis-(2-methoxy-5-trifluoromethoxybenzyl)imidazolidin-2-ylideneamine;
or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkoxy group designates "—O-alkyl, wherein alkyl is as defined above. A preferred alkoxy group of the invention is methoxy.

In the context of this invention an N-alkyl-amino group represents a secondary amino group, and an N,N-dialkyl-amino group represents a tertiary amino group, wherein alkyl is as defined above.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxy group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Isomers

It will be appreciated by those skilled in the art that the compounds of the present invention may exist in different stereoisomeric forms, including enantiomers, diastereomers, as well as geometric isomers (cis-trans isomers). The invention includes all such isomers and any mixtures thereof including racemic mixtures.

Racemic forms can be resolved into the optical antipodes by known methods and techniques. One way of separating the enantiomeric compounds (including enantiomeric intermediates) is by use of an optically active acid and liberating the diastereomeric resolved salt by treatment with a base. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates, or camphorsulphonate) salts for example.

Additional methods for the resolving the optical isomers are known in the art. Such methods include those described by Jaques J, Collet A, & Wilen S in *Enantiomers, Racemates, and Resolutions*", John Wiley and Sons, New York (1981).

Optical active compounds can also be prepared from optical active starting materials or intermediates.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to modulate SK channels in vitro. Functional modulation can be determined by measuring the compound-induced change in SK current by the patch clamp technique as described in e.g. Strøbaek et al.: "Pharmacological characterization of small-conductance $Ca^{2+}$-activated K channels expressed in HEK293 cells", British Journal of Pharmacology 2000 129 991-999. From this type of measurements the potency of a given compound can be determined as e.g. $K_i$ or $IC_{50}$ values for blockers/inhibitors and $EC_{50}$ values for openers/activators. Similar data can be obtained from other patch clamp configurations and from channels expressed endogenously in various cell lines.

In one embodiment, the compounds of the invention show selectivity for SK3 over SK1 and SK2. In a further embodiment, the compounds of the invention are positive SK channel modulators, such as positive SK3 channel modulators. In a still further embodiment, the compounds of the invention are negative modulators, such as negative SK3 channel modulators. In a special embodiment, the compounds of the invention are SK channel blockers, such as SK3 channel blockers.

Based on the activity observed in the patch clamp experiments, the compound of the invention is considered useful for the treatment, prevention or alleviation of a disease or a disorder or a condition of a mammal, including a human, which disease, disorder or condition is responsive to modulation of SK channels.

In a special embodiment, the compounds of the invention are considered useful for the treatment, prevention or alleviation of a respiratory disease, epilepsy, convulsions, seizures, absence seizures, vascular spasms, coronary artery spasms, motor neuron diseases, myokymia, renal disorders, polycystic kidney disease, bladder hyperexcitability, bladder spasms, urinogenital disorders, urinary incontinence, bladder outflow obstruction, erectile dysfunction, gastrointestinal dysfunction, gastrointestinal hypomotility disorders, gastrointestinal motility insufficiency, postoperative ileus, constipation, gastroesophageal reflux disorder, secretory diarrhea, ischaemia, cerebral ischaemia, ischaemic heart disease, angina pectoris, coronary heart disease, ataxia, traumatic brain injury, stroke, Parkinson's disease, bipolar disorder, psychosis, schizophrenia, anxiety, mood disorders, depression, manic depression, psychotic disorders, dementia, learning deficiencies, age related memory loss, memory and attention deficits, Alzheimer's disease, amyotrophic lateral sclerosis (ALS), dysmenorrhea, narcolepsy, sleeping disorders, sleep apnea, Reynaud's disease, intermittent claudication, Sjorgren's syndrome, xerostomia, arrhythmia, cardiovascular disorders, hypertension, myotonic dystrophy, myotonic muscle dystrophia, spasticity, xerostomi, diabetes Type II, hyperinsulinemia, premature labour, cancer, brain tumors, inflammatory bowel disease, irritable bowel syndrome, colitis, colitis Crohn, immune suppression, hearing loss, migraine, pain, neuropathic pain, inflammatory pain, trigeminal neuralgia, vision loss, rhinorrhoea, ocular hypertension (glaucoma), and baldness.

In a more preferred embodiment, the compounds of the invention are considered useful for the treatment, prevention or alleviation of a respiratory disease, urinary incontinence, erectile dysfunction, anxiety, epilepsy, psychosis, schizophrenia, bipolar disorder, depression, amyotrophic lateral sclerosis (ALS), Parkinson's disease or pain.

In an even more preferred embodiment, the compounds of the invention are considered useful for the treatment, prevention or alleviation of psychosis, schizophrenia, bipolar disorder, depression, epilepsy, Parkinson's disease or pain.

In a still more preferred embodiment, the compounds of the invention are considered useful for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In another more preferred embodiment, the compounds of the invention are considered useful for the treatment, prevention or alleviation of schizophrenia, depression or Parkinson's disease.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the guanidine derivative of the invention.

The guanidine derivative may in particular be
1,3-Bis-(3,4-difluorobenzyl)imidazolidin-2-ylideneamine;
1,3-Bis-(3,4-dichlorobenzyl)imidazolidin-2-ylideneamine;
1,3-Dibenzyl-imidazolidin-2-ylideneamine;
1,3-Bis-(3,4-difluorobenzyl)-3,4-dihydro-1H-quinazolin-2-ylideneamine;
(±)-trans-1,3-Bis-(3,4-difluoro-benzyl)octahydro-benzoimidazol-2-ylideneamine;
1,3-Bis-(4-fluorobenzyl)imidazolidin-2-ylideneamine;
1,3-Bis-(3,4-difluorobenzyl)tetrahydropyrimidin-2-ylideneamine;
1,3-Bis-(3-trifluoromethyl-benzyl)imidazolidin-2-ylideneamine;
1,3-Bis-(2-bromo-4,5-difluorobenzyl)-3,4-dihydro-1H-quinazolin-2-ylideneamine;
1,3-Bis-(2-bromo-4,5-difluorobenzyl)imidazolidin-2-ylideneamine;
1-(3,4-Difluorobenzyl)-3-phenyl-imidazolidin-2-ylideneamine;
1,3-Bis-(2,4,5-trifluorobenzyl)imidazolidin-2-ylideneamine;
1,3-Bis-(3,4-difluorobenzyl)-[1,3]diazepan-2-ylideneamine;
1,3-Bis-(3-trifluoromethoxybenzyl)imidazolidin-2-ylideneamine; or
1,3-Bis-(2-methoxy-5-trifluoromethoxybenzyl)imidazolidin-2-ylideneamine;

or a pharmaceutically acceptable salt thereof.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be prepared by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of SK channels, and which method comprises administering to such a living animal body, including a human, in need thereof an effective amount of a chemical compound of the invention.

The preferred medical indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

The procedures represent generic procedures used to prepare compounds of the invention. Abbreviations used are as follows:
Ac: acetyl
Boc: tert-butyloxycarbonyl
DMF: N,N-dimethylformamide
Et: ethyl
eq: equivalent(s)
LCMS: liquid chromatography mass spectrometry
LDA: lithium diisopropylamine
Me: methyl
mp: melting point
MW: microwave
rt: room temperature
TEA: triethylamine
THF: tetrahydrofuran Procedure A To the required diamine dissolved in dichloromethane was added aqueous 1M NaHCO₃ (3 eq) and di-tert-butyl-dicarbonate (2 eq) and the mixture stirred at rt for 4 hours. The organic phase was isolated, washed with 0.1 M aqueous HCl, dried with MgSO₄, filtered and evaporated to dryness to give the N,N'-diBoc protected diamine.

In the second step, the N,N'-diBoc protected diamine was dissolved in THF and added dropwise under nitrogen to a solution of 2.2 eq LDA in THF at −78° C. The reaction mixture was allowed to warm slowly to 0° C. and the required benzyl halide (2.2 eq) was added dropwise. The mixture was stirred at rt under nitrogen overnight, added aqueous NaHCO₃ and extracted with EtOAc. The combined organic phases were dried (MgSO₄), filtered, concentrated in vacuo and the crude product purified by column chromatography (EtOAc/hexane) to give the N,N'-dibenzylated N,N'-diBoc diamine intermediate.

In the subsequent step, the N,N'-dibenzyl-N,N'-diBoc diamine was dissolved in dichloromethane and added 20 eq of trifluoroacetic acid and stirred two hours at rt. The reaction mixture was then evaporated to dryness, added aqueous NaHCO₃ and extracted with dichloromethane. The combined organic phase was dried (MgSO₄), filtered and concentrated to dryness to give the desired N,N'-dibenzylated diamine.

In the last step, the N,N'-dibenzylated diamine was dissolved in acetonitrile and added cyanogen bromide (1.4 eq). The mixture was stirred at room temperature and the formed precipitate was filtered off and washed with acetonitril to give the desired 1,3-dibenzylated guanidine derivative. Alternatively, this product was purified by column chromatography, preparative LCMS or by recrystallization.

An example of Procedure A, the preparation of 1,3-bis-(3,4-difluorobenzyl)-imidazolidin-2-ylideneamine, is shown in Scheme 1.

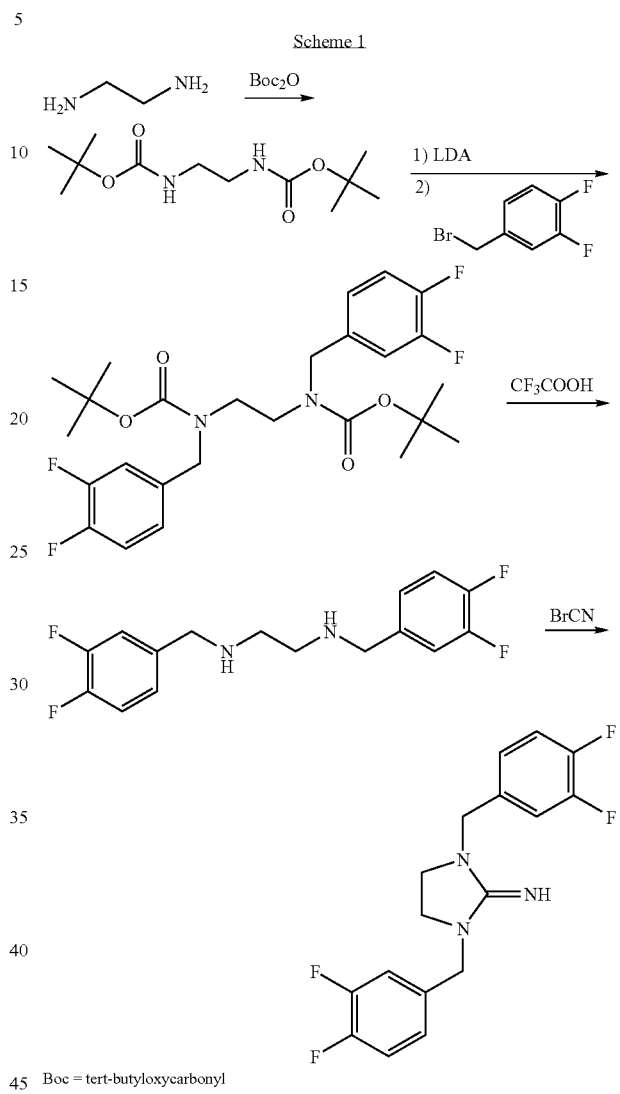

Boc = tert-butyloxycarbonyl

Procedure B

In the first step, the required diamine dissolved in dioxane was added di-tert-butyl-dicarbonate (2 eq) and the mixture stirred at 90° C. overnight. After cooling to room temperature the reaction mixture was evaporated to dryness and the crude product used without further purification in the next step.

The N,N'-di-Boc protected diamine was dissolved in DMF, cooled to 0° C. and added 2 eq of sodium hydride. The reaction mixture was stirred 1 hour at 0° C. and the required benzyl halide (2 eq) was added dropwise. The mixture was stirred at room temperature under nitrogen for two hours, added aqueous NaHCO₃ and extracted with EtOAc. The combined organic phase was dried (MgSO₄), filtered, concentrated in vacuo and the crude product purified by column chromatography (EtOAc/hexane) to give the desired N,N'-dibenzylated N,N'-diBoc diamine.

In the subsequent step, the N,N'-dibenzylated N,N'-diBoc diamine was dissolved in dichloromethane, cooled to 0° C., added 10 eq of trifluoroacetic acid and stirred overnight at room temperature. The reaction mixture was evaporated to dryness, redissolved in EtOAc, added aqueous 1M NaOH and extracted with EtOAc. The combined organic phases were dried (Na$_2$SO$_4$), filtered and evaporated to dryness to give the desired N,N'-dibenzylated diamine.

In the last step, the N,N'-dibenzylated diamine was dissolved in ethanol and added cyanogen bromide (1.1 eq). The mixture was stirred at 0° C. for one hour followed by heating to reflux temperature for 4 hours. After cooling to rt, the mixture was evaporated to dryness and the crude 1,3-dibenzylated guanidine derivative was purified by column chromatography, preparative LCMS or by recrystallization.

An example of Procedure B, the preparation of 1,3-bis-(3,4-difluorobenzyl)-3,4-dihydro-1H-quinazolin-2-ylideneamine, is shown in Scheme 2.

then added sodium triacetoxyborohydride (3 eq) and stirred at room temperature for two days and an additional 16 hours at 40° C. The reaction mixture was cooled to rt, added water and extracted with EtOAc. The combined organic phase was washed with brine, dried (Na$_2$SO$_4$), filtered and concentrated in vacuo. The crude product was then purified by column chromatography (EtOAc/hexane) to give the desired N,N'-dibenzylated diamine.

The N,N'-dibenzylated diamine was dissolved in ethanol and reacted with cyanogen bromide (1.1 eq) and purified as described in Procedure A, to give the desired 1,3-dibenzylated guanidine derivative.

An example of Procedure C, the preparation of (±)-trans-1,3-bis-(3,4-difluoro-benzyl)octahydrobenzoimidazol-2-ylideneamine, is shown in Scheme 3.

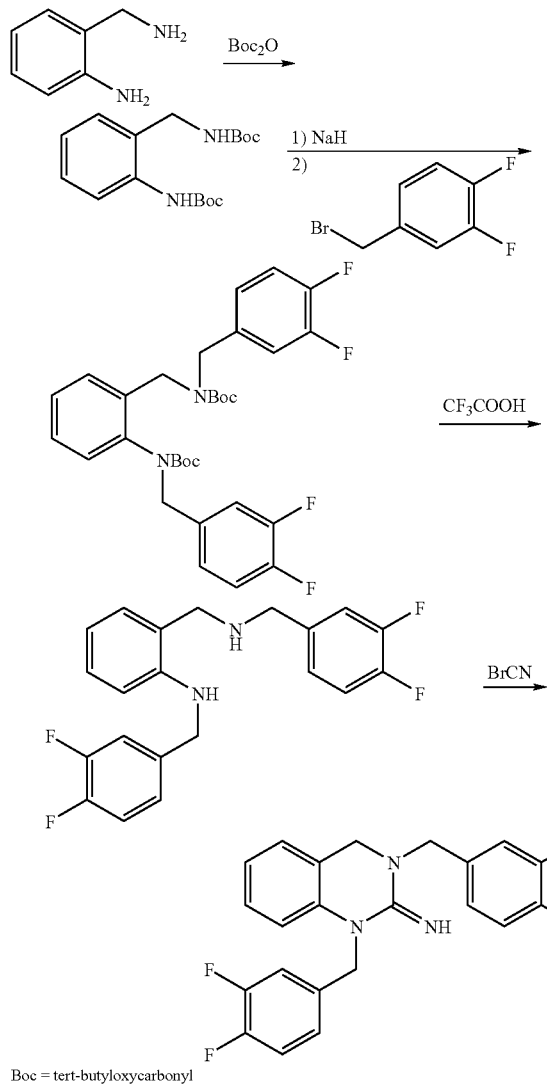

Scheme 2

Boc = tert-butyloxycarbonyl

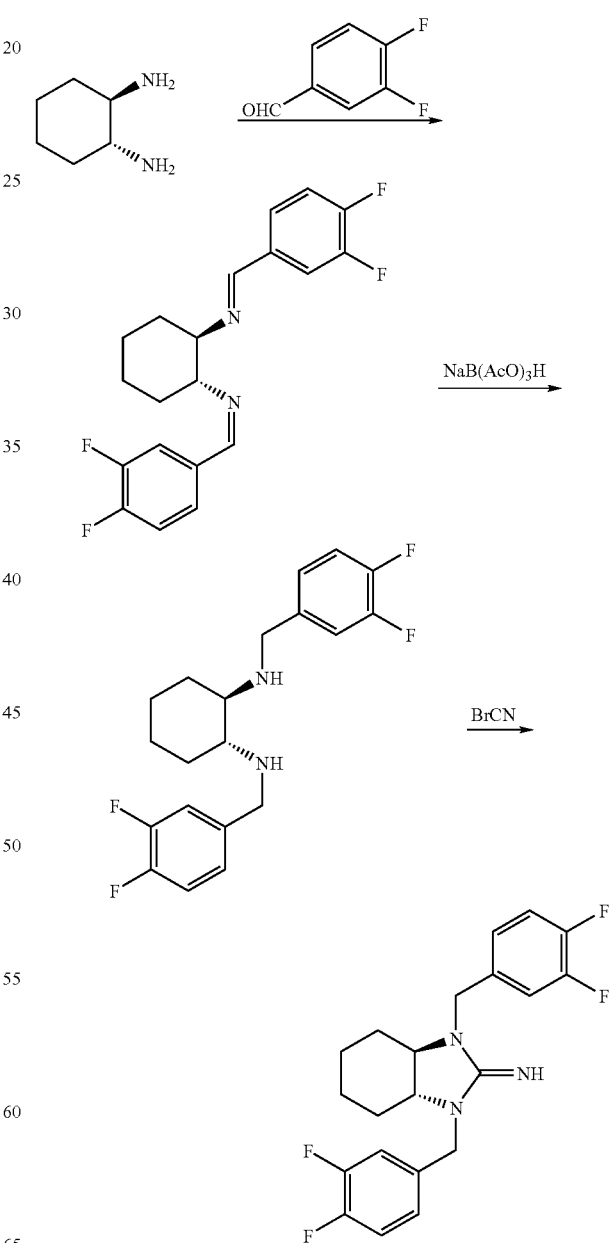

Scheme 3

Procedure C

To the required diamine dissolved in THF was added a benzaldehyde (2 eq), heated to reflux and the formed water was removed by use of a Dean Stark apparatus. Thus, the reaction mixture was stirred at reflux temperature overnight, cooled to room temperature and evaporated to dryness. The remaining crude imine was redissolved in dichloromethane, added molecular sieves and cooled to 0° C. The mixture was

Procedure D

The required diamine was converted into the corresponding diamide by reacting via one of several standard methods with an activated carboxylic acid derivative (2 eq), such as a benzoyl halide, a carboxylic acid anhydride or a carboxylic acid which has been activated in situ using a peptide coupling reagent like dicyclohexylcarbodiimide. In the second step, the diamide was dissolved in THF, cooled to 0° C. and added a solution of borane in THF (8 eq). The reaction mixture was stirred under nitrogen at rt for one hour and subsequently heated to 40° C. overnight. The mixture was cooled to rt, added 1M aqueous NaOH and extracted with EtOAc. The combined organic phases were washed with brine, dried ($Na_2SO_4$), filtered and concentrated in vacuo. The crude product was then purified by column chromatography (EtOAc/hexane) to give the desired N,N'-dialkylated diamine.

The N,N'-dialkylated diamine was dissolved in ethanol and reacted with cyanogen bromide (1.1 eq) and purified as described in Procedure A, to give the desired 1,3-dialkylated guanidine derivative.

An example of Procedure D, the preparation of 1,3-bis-(2-bromo-4,5-difluorobenzyl)-3,4-dihydro-1H-quinazolin-2-ylideneamine, is shown in Scheme 4.

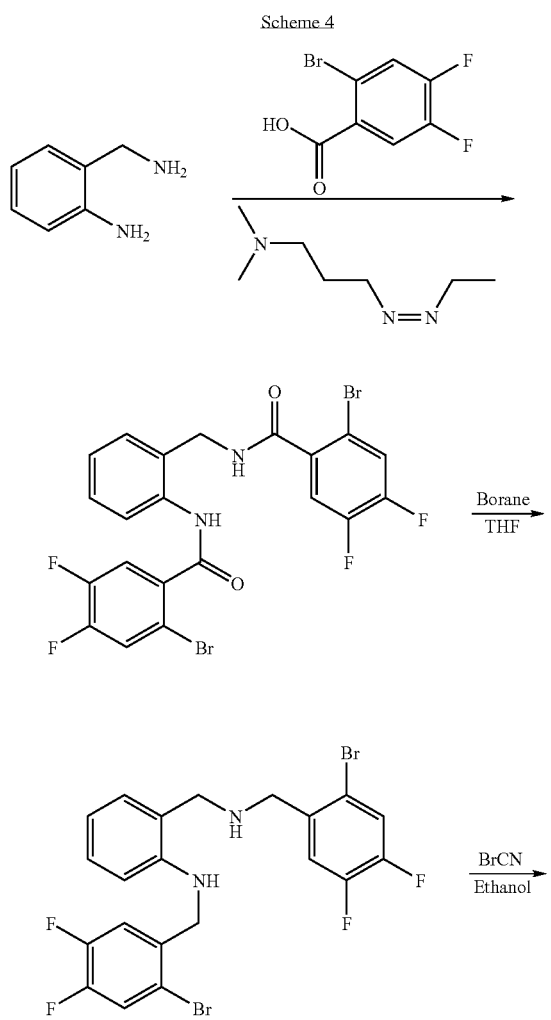

Scheme 4

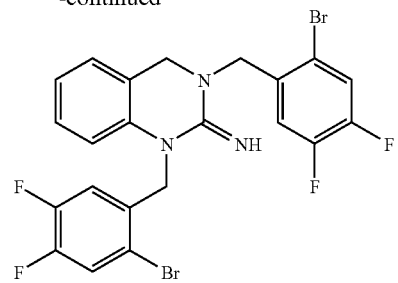

Example 1

1,3-Bis-(3,4-difluorobenzyl)imidazolidin-2-ylidene-amine (Compound 1)

The title compound was prepared in four steps by Procedure A, using 3,4-difluorobenzyl bromide as benzylating reagent. After reacting with cyanogen bromide, the precipitated solid was filtered off and washed with acetonitril to give the title compound as the hydrogen bromide salt. $^1$NMR (DMSO-d6) δ 3.51 (s, 4H), 4.58 (s, 4H), 7.21-7.24 (m, 2H), 7.46-7.54 (m, 4H), 8.47 (s, 2H). MS (ES$^+$) m/z 338 ([M+1]$^+$, 100).

Example 2

1,3-Bis-(3,4-dichlorobenzyl)imidazolidin-2-ylidene-amine (Compound 2)

The title compound was prepared in four steps by Procedure A, using 3,4-dichlorobenzyl bromide as benzylating reagent. After reacting with cyanogen bromide, the precipitated solid was filtered off and the crude material purified by preparative LCMS to give the title compound as the hydrogen bromide salt. $^1$NMR (DMSO-d6) δ 3.50 (s, 4H), 4.58 (s, 4H), 7.31-7.35 (m, 2H), 7.62-7.71 (m, 4H), 8.45 (s, 2H). MS (ES$^+$) m/z 404 ([M+1]$^+$, 100).

Example 3

Dibenzyl-imidazolidin-2-ylideneamine (Compound 3)

The title compound was prepared in one step from N,N'-dibenzylethylenediamine and cyanogen bromide as described in Procedure A. The precipitated solid was filtered off the reaction mixture, washed with acetonitrile and recrystallized from MeOH to give the title compound as a hydrogen bromide salt. $^1$NMR (DMSO-d6) δ 3.48 (s, 4H), 4.61 (s, 4H), 7.32-7.46 (m, 10H), 8.51 (s, 2H). MS (ES$^+$) m/z 266 ([M+1]$^+$, 100).

Example 4

1,3-Bis-(3,4-difluorobenzyl)-3,4-dihydro-1H-quinazolin-2-ylideneamine (Compound 4)

The title compound was prepared from 2-aminobenzylamine in four steps by Procedure B, using 3,4-difluorobenzyl bromide as benzylating reagent, and isolated as the hydrogen bromide salt (mp 215-218° C.). $^1$NMR (DMSO-d6) δ 4.55 (s, 2H), 4.90 (s, 2H), 5.28 (s, 2H), 7.08-7.58 (m, 10H), 8.53 (s, 2H). MS (ES$^+$) m/z 400 ([M+1]$^+$, 100).

Example 5

(±)-trans-1,3-Bis-(3,4-difluoro-benzyl)octahydro-benzoimidazol-2-ylideneamine (Compound 5)

The title compound was prepared from (±)-trans-1,2-cyclohexanediamine and 3,4-difluorobenzaldehyde by Procedure C. After reacting with cyanogen bromide, the reaction mixture was evaporated to dryness and the crude product washed with ether and recrystallized from MeOH to give the title compound as the hydrogen bromide salt (mp 238-240° C.). MS (ES$^+$) m/z 392 ([M+1]$^+$, 100).

Example 6

1,3-Bis-(4-fluorobenzyl)imidazolidin-2-ylideneamine (Compound 6)

The title compound was prepared in four steps by Procedure A, using 4-fluorobenzyl bromide as benzylating reagent. After reacting with cyanogen bromide, the precipitated solid was filtered off and washed with acetonitril to give the title compound as a hydrogen bromide salt. $^1$NMR (DMSO-d6) δ 3.46 (s, 4H), 4.60 (s, 4H), 7.23-7.31 (m, 4H), 7.36-7.43 (m, 4H), 8.55 (s, 2H). MS (ES$^+$) m/z 302 ([M+1]$^+$, 100).

Example 7

1,3-Bis-(3,4-difluorobenzyl)tetrahydropyrimidin-2-ylideneamine (Compound 7)

The title compound was prepared in four steps by Procedure A, using 4-fluorobenzyl bromide as benzylating reagent. After reacting with cyanogen bromide, the reaction mixture was filtered, evaporated and the remaining crude product recrystallized from Et$_2$O/acetonitrile to give the title compound as the hydrogen bromide salt. $^1$NMR (DMSO-d6) δ 1.97 (p, 2H), 3.36 (t, 4H), 4.66 (s, 4H), 7.15-7.20 (m, 2H), 7.38-7.54 (m, 4H), 7.60 (br s, 2H). MS (ES$^+$) m/z 352 ([M+1]$^+$, 100).

Example 8

1,3-Bis-(3-trifluoromethyl-benzyl)imidazolidin-2-ylideneamine (Compound 8)

The title compound was prepared in four steps by Procedure A, using 3-(trifluoromethyl)benzyl bromide as benzylating reagent. After reacting with cyanogen bromide, the precipitated solid was filtered off and recrystallized from acetonitril to give the title compound as a hydrogen bromide salt. $^1$NMR (DMSO-d6) δ 3.54 (s, 4H), 4.73 (s, 4H), 7.65-7.78 (m, 8H), 8.60 (s, 2H). MS (ES$^+$) m/z 402 ([M+1]$^+$, 100).

Example 9

1,3-Bis-(2-bromo-4,5-difluorobenzyl)-3,4-dihydro-1H-quinazolin-2-ylideneamine (Compound 9)

The title compound was prepared in three steps as described in Procedure D. In the first step, 2-amino-benzylamine was reacted in DMF with 2-bromo-4,5-difluorobenzoic acid (2 eq) in the presence of N-ethyl-N'-(3-dimethylaminopropyl)-carbodiimide (2.2 eq) and 1-hydroxy-7-azabenzo-triazole, to give the dibenzoylated diamine. After the last step (reaction with cyanogen bromide), the precipitated solid was filtered off and recrystallized to give the title compound as the hydrogen bromide salt (Mp. 220-224° C.). MS (ES$^+$) m/z 558 ([M+1]$^+$, 100).

Example 10

1,3-Bis-(2-bromo-4,5-difluorobenzyl)imidazolidin-2-ylideneamine (Compound 10)

The title compound was prepared in three steps as described in Procedure D. In the first step, ethylenediamine was reacted in DMF with 2-bromo-4,5-difluorobenzoic acid (2 eq) in the presence of N-ethyl-N'-(3-dimethylamino-propyl)carbodiimide (2.2 eq) and 1-hydroxybenzotriazole, to give the dibenzoylated diamine. After the last step (reaction with cyanogen bromide), the crude product was isolated upon aqueous work-up and purified by column chromatography (CH$_2$Cl$_2$/MeOH) to give the title compound as the free base. $^1$NMR (DMSO-d6) δ 3.61 (s, 4H), 4.73 (s, 4H), 7.63-7.71 (m, 2H), 7.98-8.01 (m, 2H), 8.42 (br s, 1H). MS (ES$^+$) m/z 496 ([M+1]$^+$, 100).

Example 11

1-(3,4-Difluorobenzyl)-3-phenyl-imidazolidin-2-ylideneamine (Compound 11)

The title compound was prepared from N-phenylethylenediamine in four steps by Procedure A. In the first step, one equivalent of Boc$_2$O was used and, similarly, one equivalent of 3,4-difluorobenzyl bromide was used as benzylating reagent in the second step. After reacting with cyanogen bromide, the crude product was isolated upon aqueous workup and purified by preparative LCMS to give the title compound as the free base. MS (ES$^+$) m/z 288 ([M+1]$^+$, 100); HR-MS: 288.1316 ([M+1]$^+$, C$_{16}$H$_{16}$F$_2$N$_3$; calc. 288.131228).

Example 12

1,3-Bis-(2,4,5-trifluorobenzyl)imidazolidin-2-ylideneamine (Compound 12)

The title compound was prepared in three steps as described in Procedure D. In the first step, ethylenediamine was reacted in acetonitrile with 2,4,5-trifluorobenzoylchloride (2 eq) in the presence of TEA to give the N,N'-dibenzoylated ethylenediamine upon aqueous work-up. After the last step (reaction with cyanogen bromide, performed at 200° C. for 60 min using MW heating), the precipitated solid was filtered off and recrystallized to give the title compound as the hydrogen bromide salt. MS (ES$^+$) m/z 374 ([M+1]$^+$, 100); HR-MS: 374.1086 ([M+1]$^+$, C$_{17}$H$_{14}$F$_6$N$_3$; calc. 374.10919).

Example 13

1,3-Bis-(3,4-difluorobenzyl)-[1,3]diazepan-2-ylideneamine (Compound 13)

The title compound was prepared from 1,4-diaminobutane in four steps by Procedure A, using 3,4-difluorobenzyl bromide as benzylating reagent. After reacting with cyanogen bromide (this step performed at 200° C. for 60 min using MW heating), the crude product was isolated upon aqueous work-up and purified by preparative LCMS to give the title compound as the free base. MS (ES$^+$) m/z 366 ([M+1]$^+$, 100); HR-MS: 366.1599 ([M+1]$^+$, C$_{19}$H$_{20}$F$_4$N$_3$; calc. 366.159334).

Example 14

1,3-Bis-(3-trifluoromethoxybenzyl)imidazolidin-2-ylideneamine (Compound 14)

The title compound was prepared in three steps as described in Procedure D. In the first step, ethylenediamine was reacted in acetonitrile with 3-(trifluoromethoxy)benzoylchloride (2 eq) in the presence of TEA to give the N,N'-dibenzoylated ethylenediamine upon aqueous work-up. After the last step (reaction with cyanogen bromide), the crude product was isolated upon aqueous work-up, recrystallized from diethyl ether and the title compound isolated as the hydrogen bromide salt. MS (ES$^+$) m/z 434 ([M+1]$^+$, 100); HR-MS: 434.1299 ([M+1]$^+$, $C_{19}H_{18}F_6N_3O_2$; calc. 434.13032).

Example 15

1,3-Bis-(2-methoxy-5-trifluoromethoxybenzyl)imidazolidin-2-ylideneamine (Compound 15)

The title compound was prepared in three steps as described in Procedure D. In the first step, ethylenediamine was reacted in acetonitrile with 2-methoxy-5-(trifluoromethoxy)benzoylchloride (2 eq) in the presence of TEA to give the dibenzoylated ethylenediamine upon aqueous work-up. After the last step (reaction with cyanogen bromide), the crude product was isolated upon aqueous work-up and purified by column chromatography to give the title compound as the hydrogen bromide salt. MS (ES$^+$) m/z 494 ([M+1]$^+$, 100); HR-MS: 494.1532 ([M+1]$^+$, $C_{21}H_{22}F_8N_3O_4$; calc. 494.15145).

Example 16

Biological Activity

This example demonstrates the biological activity of a compound representative of the invention. The ionic current through small-conductance Ca$^{2+}$-activated K$^+$ channels (SK channels, subtype 3) was recorded using the whole-cell configuration of the patch-clamp technique.

HEK293 tissue culture cells expressing hSK3 channels were grown in DMEM (Dulbecco's Modified Eagle Medium) supplemented with 10% FCS (foetal calf serum) at 37° C. in 5% CO$_2$. At 60-80% confluency, cells were harvested by trypsin treatment and seeded on cover slips.

Cells plated on coverslips were placed in a 15 μl perfusion chamber (flowrate ~1 ml/min) mounted on an inverted microscope placed on a vibration-free table in a grounded Faraday cage. The experiments were performed at room temperature (20-22° C.). The EPC-9 patch-clamp amplifier (HEKA-electronics, Lambrect, Germany) was connected to a Macintosh computer via an ITC16 interface. Data were stored directly on the hard-disk and analysed by IGOR software (Wavemetrics, Lake Oswega, Oreg., USA).

The whole-cell configuration of the patch-clamp technique was applied. In short: The tip of a borosilicate pipette (resistance 2-4 MΩ) is gently placed on the cell membrane using remote control systems. Light suction results in the formation of a giga seal (pipette resistance increases to more than 1 GΩ) and the cell membrane underneath the pipette is then ruptured by more powerful suction. Cell capacitance was electronically compensated and the resistance between the pipette and the cell interior (the series resistance, Rs) was measured and compensated for. The cell capacitances ranged from 5 to 20 pF, and the series resistance was in the range 3 to 6 MΩ. Rs—as well as capacitance compensation were updated during the experiments (before each stimulus). Leak-subtractions were not performed.

The extracellular (bath) solution contained (in mM): 156 KCl, 0.1 CaCl$_2$, 3 MgCl$_2$, 10 HEPES (pH=7.4 with KOH). The test compound was dissolved in DMSO and then diluted at least 1000 times in the extracellular solution.

The intracellular (pipette) solution contained: 154 mM KCl, 10 mM HEPES, 10 mM EGTA. Concentrations of CaCl$_2$ and MgCl$_2$ needed to obtain the desired free concentrations of Ca$^{2+}$ (0.3-0.4 μM, Mg$^{2+}$ always 1 mM) were calculated by EqCal software (Cambridge, UK) and added.

After establishment of the whole-cell configuration, voltage-ramps (−80 to +80 mV) were applied to the cell every 5 seconds from a holding potential of 0 mV. A stable baseline current was obtained within a period of 100-500 seconds, and the compound was then added by changing to an extracellular solution containing the test compound. Activity was quantified from the change in current at −75 mV.

For inhibitors a K$_d$ value, defined as the concentration required for decreasing the baseline current to 50% of the initial current, was estimated.

The K$_d$ values determined for Compound 7 and Compound 15, considered representative of the compounds of the invention, are in the sub-micromolar range (i.e. below 1 μM), which is an indication of their strong SK3 activating properties.

The invention claimed is:
1. A guanidine derivative of Formula I:

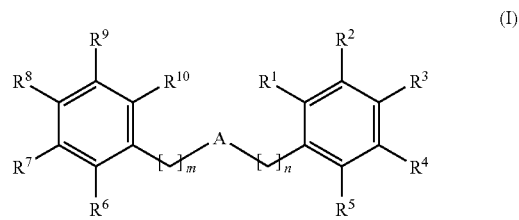

(I)

a stereoisomer thereof or any mixture of its stereoisomers, or a pharmaceutically acceptable salt thereof; wherein
m and n, independently of each other, is 0, 1 or 2,
provided, however, if m is 0 then n is not also 0;
A represents a linking group selected from II, III and IV:

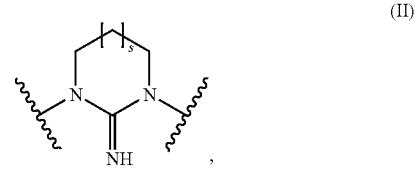

(II)

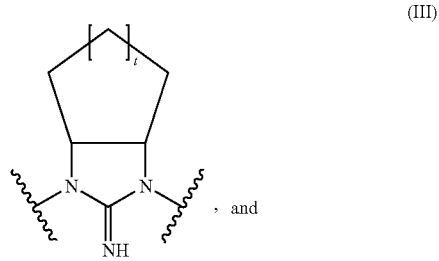

(III)

, and

-continued

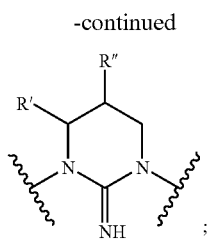
(IV)

wherein
s is 0, 1 or 2;
t is 1, 2 or 3;
R' and R" together with the ring to which they are attached form a 6-membered fused benzo ring, which benzo ring may optionally be substituted one or more times with substituents selected from the group consisting of halo, trifluoromethyl, trifluoromethoxy, cyano, alkyl, hydroxy, alkoxy, N-alkyl-amino and N,N-dialkyl-amino; and
$R^1$, $R^2$, $R^3$, $R^4$, $R^5$, $R^6$, $R^7$, $R^8$, $R^9$ and $R^{10}$, independently of each other, represent hydrogen, halo, trifluoromethyl, trifluoromethoxy, cyano, alkyl, hydroxy, alkoxy, N-alkyl-amino and/or N,N-dialkyl-amino,
provided, however, that if A is a linking group II wherein s is 0, then at least one of $R^1$, $R^2$, $R^3$, $R^4$ and $R^5$ is different from hydrogen, and at least one of $R^6$, $R^7$, $R^8$, $R^9$ and $R^{10}$ is different from hydrogen.

2. The guanidine derivative of claim 1, or a pharmaceutically acceptable salt thereof, wherein
m and n, independently of each other, is 0, 1 or 2,
provided, however, if m is 0 then n is not also 0.

3. The guanidine derivative of claim 1, or a pharmaceutically acceptable salt thereof, wherein
A represents a linking group selected from II, III and IV:

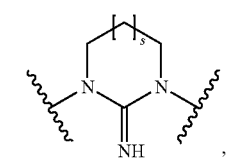
(II)

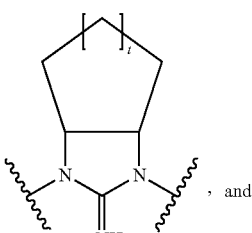
(III)
, and

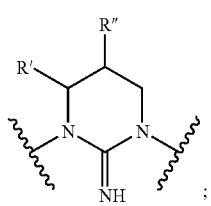
(IV)

wherein
s is 0, 1 or 2;
t is 1, 2 or 3;
R' and R" together with the ring to which they are attached form a 6-membered fused benzo ring, which benzo ring may optionally be substituted one or more times with substituents selected from the group consisting of halo, trifluoromethyl, trifluoromethoxy, cyano, alkyl, hydroxy, alkoxy, N-alkyl-amino and N,N-dialkyl-amino.

4. The guanidine derivative of claim 3, or a pharmaceutically acceptable salt thereof, wherein
A represents

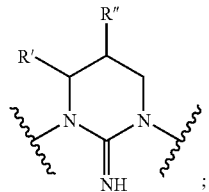

wherein
R' and R" together with the ring to which they are attached form a 6-membered fused benzo ring, which benzo ring may optionally be substituted one or more times with substituents selected from the group consisting of halo, trifluoromethyl, trifluoromethoxy, cyano, alkyl, hydroxy, alkoxy, N-alkyl-amino and N,N-dialkyl-amino.

5. The guanidine derivative of claim 1, or a pharmaceutically acceptable salt thereof, wherein
$R^1$, $R^2$, $R^3$, $R^4$, $R^5$, $R^6$, $R^7$, $R^8$, $R^9$ and $R^{10}$, independently of each other, represent hydrogen, halo, trifluoromethyl, trifluoromethoxy, cyano, alkyl, hydroxyl, alkoxy, N-alkyl-amino and/or N,N-dialkyl-amino.

6. The guanidine derivative of claim 5, or a pharmaceutically acceptable salt thereof, wherein
one of $R^1$, $R^2$, $R^3$, $R^4$ and $R^5$, and one of $R^6$, $R^7$, $R^8$, $R^9$ and $R^{10}$, independently of each other, represent halo, trifluoromethyl, trifluoromethoxy, cyano, alkyl and/or alkoxy; and
the remaining of $R^1$, $R^2$, $R^3$, $R^4$ and $R^5$, and $R^6$, $R^7$, $R^8$, $R^9$ and $R^{10}$ represent hydrogen.

7. The guanidine derivative of claim 5, or a pharmaceutically acceptable salt thereof, wherein
two of $R^1$, $R^2$, $R^3$, $R^4$ and $R^5$, and two of $R^6$, $R^7$, $R^8$, $R^9$ and $R^{10}$, independently of each other, represent halo, trifluoromethyl, trifluoromethoxy, cyano, alkyl and/or alkoxy; and
the remaining of $R^1$, $R^2$, $R^3$, $R^4$ and $R^5$, and $R^6$, $R^7$, $R^8$, $R^9$ and $R^{10}$ represent hydrogen.

8. The guanidine derivative of claim 5 or a pharmaceutically acceptable salt thereof, wherein
three of $R^1$, $R^2$, $R^3$, $R^4$ and $R^5$, and three of $R^6$, $R^7$, $R^8$, $R^9$ and $R^{10}$, independently of each other, represent halo, trifluoromethyl, trifluoromethoxy, cyano, alkyl and/or alkoxy; and
the remaining of $R^1$, $R^2$, $R^3$, $R^4$ and $R^5$, and $R^6$, $R^7$, $R^8$, $R^9$ and $R^{10}$ represent hydrogen.

9. The guanidine derivative of claim 1, which is
1,3-Bis-(3,4-difluorobenzyl)imidazolidin-2-ylideneamine;
1,3-Bis-(3,4-dichlorobenzyl)imidazolidin-2-ylideneamine;
1,3-Bis-(3,4-difluorobenzyl)-3,4-dihydro-1H-quinazolin-2-ylideneamine;

(±)-trans-1,3-Bis-(3,4-difluoro-benzyl)octahydro-benzoimidazol-2-ylideneamine;
1,3-Bis-(4-fluorobenzyl)imidazolidin-2-ylideneamine;
1,3-Bis-(3,4-difluorobenzyl)tetrahydropyrimidin-2-ylideneamine;
1,3-Bis-(3-trifluoromethyl-benzyl)imidazolidin-2-ylideneamine;
1,3-Bis-(2-bromo-4,5-difluorobenzyl)-3,4-dihydro-1H-quinazolin-2-ylideneamine;
1,3-Bis-(2-bromo-4,5-difluorobenzyl)imidazolidin-2-ylideneamine;
1-(3,4-Difluorobenzyl)-3-phenyl-imidazolidin-2-ylideneamine;
1,3-Bis-(2,4,5-trifluorobenzyl)imidazolidin-2-ylideneamine;
1,3-Bis-(3,4-difluorobenzyl)[1,3]diazepan-2-ylideneamine;
1,3-Bis-(3-trifluoromethoxybenzyl)imidazolidin-2-ylideneamine; or
1,3-Bis-(2-methoxy-5-trifluoromethoxybenzyl)imidazolidin-2-ylideneamine;
or a pharmaceutically acceptable salt thereof.

10. A pharmaceutical composition, comprising a therapeutically effective amount of the guanidine derivative of claim 1, or any of its stereoisomers or any mixture of its stereoisomers, or a pharmaceutically acceptable salt thereof, together with at least one pharmaceutically acceptable carrier, excipient or diluent.

\* \* \* \* \*

UNITED STATES PATENT AND TRADEMARK OFFICE
CERTIFICATE OF CORRECTION

Page 1 of 1

PATENT NO. : 8,048,877 B2
APPLICATION NO. : 12/279928
DATED : November 1, 2011
INVENTOR(S) : Ulrik Svane Sørensen et al.

It is certified that error appears in the above-identified patent and that said Letters Patent is hereby corrected as shown below:

ON THE TITLE PAGE:

Please insert the following Item:

-- Related U.S. Application Data
(60) Provisional application No. 60/785,372, filed March 24, 2006. --

IN THE SPECIFICATION:

At Column 1, immediately after the Title of the Invention, insert the following new paragraph:

-- This application is a National Stage application of PCT International Application No. PCT/EP2007/052747 filed on March 22, 2007, which designated the United States and which claims priority under 35 U.S.C. 119(a)-(d) on Application No. PA 2006 00421 filed in Denmark on March 24, 2006 and under 35 U.S.C. 119(e) on U.S. Provisional Application No. 60/785,372 filed on March 24, 2006. --

Signed and Sealed this
Fifteenth Day of May, 2012

David J. Kappos
*Director of the United States Patent and Trademark Office*